United States Patent [19]

Taran

[11] Patent Number: 5,551,296
[45] Date of Patent: Sep. 3, 1996

[54] METHOD AND DEVICE FOR REVEALING DEFECTS IN MATERIALS AND THEIR CONNECTIONS

[75] Inventor: Vladimir Taran, Jerusalem, Israel

[73] Assignee: System Testing Materials Ltd., Jerusalem, Israel

[21] Appl. No.: 520,174

[22] Filed: Aug. 28, 1995

Related U.S. Application Data

[63] Continuation of Ser. No. 57,765, May 7, 1993, abandoned.

[30] Foreign Application Priority Data

Mar. 17, 1993 [IL] Israel ......................................... 105085

[51] Int. Cl.$^6$ .................................................. G01N 29/04
[52] U.S. Cl. ................................................. 73/628; 73/627
[58] Field of Search ............................. 73/624, 625, 627, 73/628, 632, 637, 638

[56] References Cited

U.S. PATENT DOCUMENTS

| | | | |
|---|---|---|---|
| 2,700,895 | 2/1955 | Carson ........................................ | 73/624 |
| 4,098,129 | 7/1978 | Deblaere ...................................... | 73/624 |
| 4,170,142 | 10/1979 | Posakony et al. ........................... | 73/626 |
| 4,962,332 | 10/1990 | Rokurohta et al. .......................... | 73/632 |
| 4,995,260 | 2/1991 | Deason et al. ............................... | 73/632 |
| 5,060,651 | 10/1991 | Kondo et al. ................................ | 73/625 |
| 5,349,860 | 9/1994 | Nakano et al. .............................. | 73/624 |

FOREIGN PATENT DOCUMENTS

| | | |
|---|---|---|
| 0379229 | 7/1990 | European Pat. Off. . |
| 0404154 | 12/1990 | European Pat. Off. . |
| 3540610A1 | 5/1987 | Germany . |

Primary Examiner—Richard Chilcot
Assistant Examiner—Max Noori
Attorney, Agent, or Firm—Banner & Allegretti, Ltd.

[57] ABSTRACT

The method and the device for detecting flaws in materials and their connections comprise the radiation of ultrasonic rays and the reception of that energy after its reflection from the examined product, wherein the component which creates, radiates and receives the ultrasonic energy is comprised of a number of interconnected sub-plates. The focused energy which penetrates the metal has a special form appropriate to the type and shape of the product. The sub-plates are mechanically connected to a cylindrically-shaped base, and electrically interconnected by adjustable electronic control means which appropriately change the characteristics of the sub-plates when necessary. The bases of each sub-plate system are made of a material transparent to ultrasonic rays, for example plastic, and the contact surfaces of the bases of each of the sub-plate systems are fortified by grooves filled with a wear-resistant material. The shape of the base edge of each of the sub-plate systems is that of cylindrical surface section each sub-plate system is installed on the edge of one base and its shape is close to the shape of the base's cylindrical section surface. The surface of the base edge of each of the sub-plate systems is positioned at some angle relative to the contact surface of that base. One version of the device for detecting flaws in materials and their connections comprises two separate converters, each with its own cover and both connected into one unit by means of a holder and bridges. The connection between one of the converters, for example the radiator, and the holder, is made by means of a fixed bridge, while the connection between the second converter, for example the receiver, and the holder is established by means of a bridge with a hinge which allows limited movement.

50 Claims, 2 Drawing Sheets

METHOD AND DEVICE FOR REVEALING DEFECTS IN MATERIALS AND THEIR CONNECTIONS

This application is a continuation of application Ser. No. 08/057,765, filed May 7, 1993, now abandoned.

FIELD OF THE INVENTION

The invention belongs to the area of NDT defectoscopy, particularly the sphere of ultrasonic flaw detection and the various devices using such methods.

BACKGROUND OF THE INVENTION

A great deal of importance has been attached to resolving problems of quality and reliability in the manufacture of various materials, for example steel, and particularly the connection or seams between them, formed by welding, soldering or any other method. There are many well-known methods and devices available for controlling the quality of connections between metals. The discovery of faults in structures and machines is highly important; however, existing probes/detectors are frequently inaccurate, particularly when testing "Austenite" type steel, which is comprised of relatively large granules. The sensitivity of these devices is particularly low with regard to faults in "Austenite" type steel, and the need to improve these tests has become more acute in view of the accidents which have occurred in nuclear reactors.

One of these devices is described in U.S.S.R. Inventors Certificate No. 962806. This flaw detector is based on two ultrasonic vibration converters located in a single box, wherein one converter includes a panel which radiates focused energy and the other converter includes an identical panel which receives the ultrasonic radiation reflected from the product being tested. The converter panels used for the radiation and reception of focused ultrasonic radiation are made of a piezoelectric material. The echo method enables external and hidden flaws to be revealed in complete and semi-complete products of various sizes and shapes, flaws which cannot be discovered by other means.

During the test, the device moves over the surface of the material being tested, so that the focused energy is penetrated into the mostly metal product. This device radiates focused energy into the product in the form of a series of ultrasonic impulses (short pulses separated by a relatively long interval). Reflected energy is returned to the device from the metal granules, for example, of the Austenite type, which are relatively large. As stated above, the sensitivity of the known detectors for Austenite type metal is very low, while the new device is far more sensitive and capable of discerning flaws which cannot be identified by means of current devices. If the process is completed within a reasonable period of time and in a regular fashion, then the metals and the seams between them may be considered normal. However, if any change takes place in the time required by the operation or in the form of the ultrasonic ray's reflection, this is an indication of some flaw. If a flaw falls in the way of the ultrasonic impulse—then the recorded reflected impulse carries information regarding the flaw from which the focused energy was reflected, and this information is analyzed within the device or by means of peripherals connected to it. Thus, the time elapsing from the transmission of an impulse to the reception of the reflected impulse, indicates the distance between the device and the flaw; the size of the reflected impulse indicates the size of the flaw.

In the instruments currently in use, the converter panels are made of a single piece of a piezoelectric material, either straight or curved, and their parameters is the fact that at various points along the length and breadth of the panel they have different magnitude. Thus, different points of these panels have non-uniform electric and mechanical parameters, and the magnitude of certain parameters at one point can be greater by hundreds of percents than its value at another point on the same panel. This leads to tremendous difficulties in the manufacture of such devices, with the consequence that a high percentage of these devices are flawed immediately following their assembly at the plant (usually, more than 50%). As noted, one drawback of the probes/detectors in current use is their complex production, particularly given that the piezoelectric panels are shaped as part of a cylindrical surface. Because of the relative large required size of the piezoelectric panel, its mechanical and electric parameters at various points are unequal and this creates difficulties in the design of the probes characteristics. The inventors are not aware of any device capable of resolving these problems, with the exception of the device detailed below.

SUMMARY OF THE INVENTION

The method and the device for detecting flaws in materials and their connections comprise the radiation of ultrasonic rays and the reception of that energy after its reflection from the examined product, wherein the component which creates and radiates the ultrasonic-energy is comprised of a number of interconnected sub-plates. The focused energy which penetrates the metal has a special form appropriate to the type and shape of the product. The sub-plates are mechanically connected to a cylindrically-shaped base, and electrically interconnected by adjustable electronic control means which appropriately change the characteristics of the sub-plates when necessary. One version of the device for detecting flaws in materials and their connections comprises two separate converters, each with its own cover, and both connected into one unit by means of a holder and bridges. The connection between one of the converters, for example the radiator, and the holder, is made by means of a fixed bridge, while the connection between the second converter, for example the receiver, and the holder, is established by means of a bridge with a hinge which allows limited movement.

BRIEF DESCRIPTION OF THE DRAWINGS

The invention is illustrated by means of a number of drawings.

DETAILED DESCRIPTION OF THE INVENTION

Figure 1:
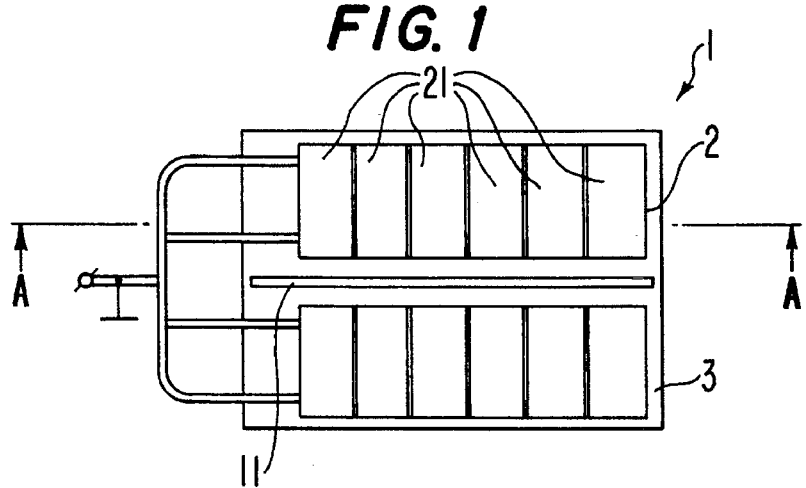
FIG. 1 is a general view of the probe/detector, view from the top.

FIG. 1 describes the ultrasonic flaw probe/detector (1) which comprises two systems (2,3) of sub-panels (21,31), where each system constitutes a converter of ultrasonic vibrations. One system (2) constitutes a focusing ultrasonic radiator, and the second system (3) comprises a panel which receives the radiation from the first panel (2). The two systems must be separated from each other, for example, by means of an ultrasonic shutter (11). Each system of sub-plates (21,31) constitutes a series of straight, (planar) square or rectangular, surfaces, fixed to a single base (22,32) and shaped in the form of a cylindrical surface segment, wherein the sub-panels combine to form an active board (2 or 3) whose shape is close to the form of the base's cylindrical segment (22) (see FIG. 2).

The two bases (22, 32) onto which the piezoelectric panels are fixed (21, 31) are a transparent ultrasonic body, for example, a prism. The energy penetrates the product through one of the bases (22), and the energy reflected through the second base (32) reaches the panel of sub-plates (32) which comprise the receiver component (3). The base (22,32) is a central part of the acoustic focusing system which is intended to focus the ultrasonic energy in a certain direction or toward a certain point. The contact surface of the panel (21, 31) bases (22, 32), i.e., the prisms, are made of plastic material in most versions, and its drawback is significant abrasion wear. In order to increase the wear resistance and the service life of these devices, the bottom surface of the two bases (22,32) is fortified by the creation of grooves (24, 34), which are filled with layers (25, 35) of another material. These layers (25, 35) are made of any wear-resistant material—for example, tin, brass, plastic,—transparent to ultrasonic radiation, wherein the thickness of the layer is smaller than the wavelength of the ultrasonic radiation in the bases (22, 32).

Figure 6:
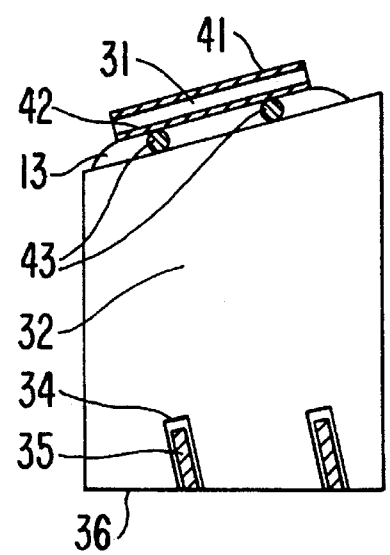
FIG. 6 is a cross-section B—B of FIG. 5, with grooves and filling of the contact surface of the probe/detector.

The sub-plates (21,31) are made of a piezoelectric material and their attachment to the base (22,32) in the above mentioned geometric form, endows the panel (2, 3) with the required ability to focus the rays. Each piezoelectric sub-plate is coated on both sides (41, 42) with a conductive cover casing intended to include it within the electrical circuit (4) (see FIG. 6). The sub-plates are attached by bonding to a base (22, 32) with geometrically-shaped edges. In the first versions of the device it was difficult to control the thickness of the bonding layer (13) between the lower coating (42) of each sub-plate (21, 31) and the base (22), and to prevent curving of the sub-plates (21, 31) relative to the base (22, 32). In order to make the thickness of the bonding layer (13) between the sub-plates (21, 31) and the base (22, 32) as uniform as possible—at least two exposed metal wires (43) are installed on the base (22, 32). Above these wires (43) is the coating (42) which is the lower conductor of each piezoelectric sub-plate (21, 31) and electrically connected to the grounding. The surface of the base (22, 32) of each of the sub-plate systems (2, 3), on which the bonding layer (13) is placed, and which is shaped like a cylindrical segment, is placed at a certain angle to the contact surface (26, 36) of that base (22, 32).

Figure 2:
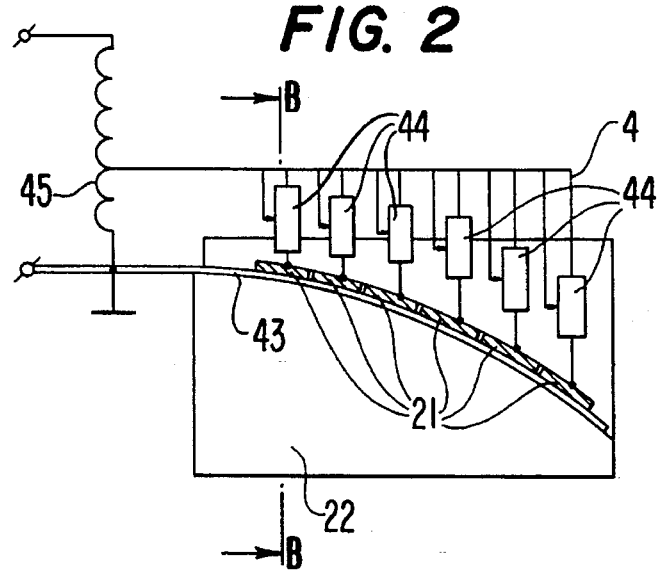
FIG. 2 is a cross-section A—A of FIG. 1 and connection of the piezoelectric panel components, both physical and electrical connection.
Figure 3:
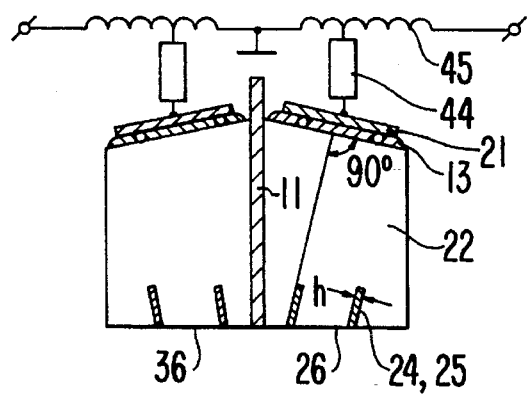
FIG. 3 is a cross-section B—B of FIG. 1 and the connections between the piezoelectric panel components.

The parameters and the properties of the sub-plate (21, 31) system (2, 3), are adjusted by electronic means (44, 45), so that each point on the panel (2, 3) is endowed with equal or variable parameters according to the requirements of the specific test. Each panel (2, 3) is connected to the electricity network by means of its own transformer (45), for example, an auto-transformer, as the upper coating (41) of each piezoelectric sub-plate (21, 31), is electrically connected by adjustable electronic means (44), for example by means of variable resistance to the mid-point of the transformer itself (45). The transformer reduces the effect of the static capacitance of the sub-plate system (2 or 3) to input parameters, and thus increases the sensitivity of the ultrasonic flaw detector (1) to a great extent. The variable resistors (44) connect and adjust each sub-plate (21, 31) separately. The sub-plates (21, 31) can be interconnected through coordinating and adjustable resistors (44) in parallel, in sequence or in groups, where the sub-plates in each group are interconnected in sequence and the groups are connected in parallel. Adjustment of the sub-plate (21, 31) parameters is carried out by electronic means, as shown in FIG. 2. The number of sub-plates (21, 31) is usually far greater than two, but even only two sub-plates permit improve the characteristics and properties of each of the systems (2, 3).

Figure 4:
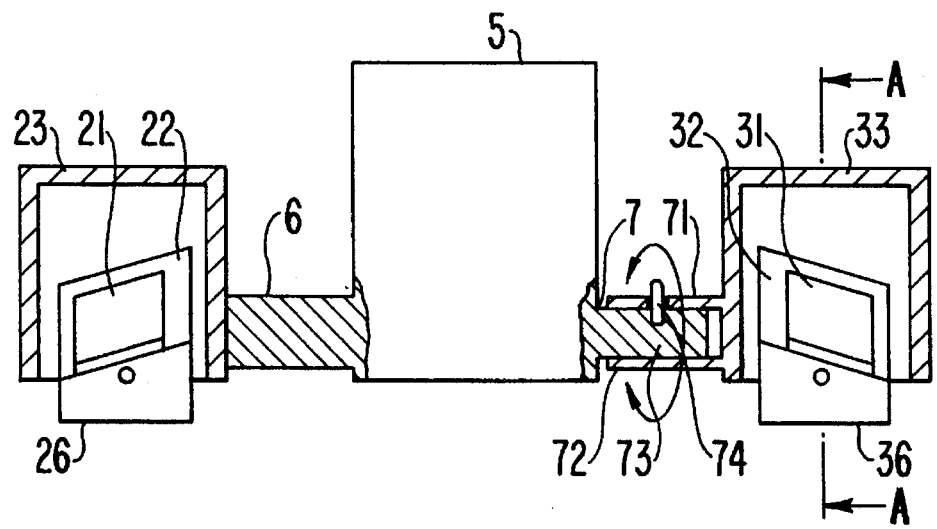
FIG. 4 is a general view of the probe/detector, where the radiator and receiver are separate.
Figure 5:
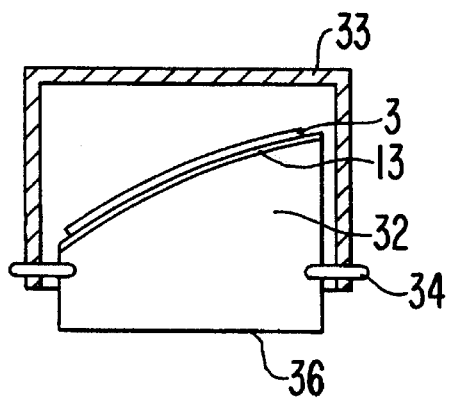
FIG. 5 is a cross-section A—A of FIG. 4

FIG. 4 describes an ultrasonic flaw probe/detector (1) in which the two converters are separated from each other, and each of them is placed within its own cover (23, 33), and they are connected into a single unit (1) by means of a holder (5). The radiating component (2) and the radiation receiving component (3) are connected to the holder (5) by means of bridges (6, 7). In the preferred version of the flaw detector (1), the connection between one of the converters, for example the radiator (2), and the holder (5) is established by means of a fixed bridge (6), while the connection between the other converter, for example the receiver (3), and the holder (5) is established by a bridge (7) with a hinge (71). The hinge (71) facilitates the performance of more accurate tests on angular and non-uniform surfaces. In the preferred version, the hinge (71) is comprised of two cylinders (72, 73) of different diameters, an external hollow cylinder (72) and an internal solid one (73). A small gap is left between the two cylinders, which allows one cylinder (73) to turn within the other (72), wherein this movement is limited by special means, for example, a rod (74) connected to one of the cylinders, for example the inner one (73), and moves within the slot of the second cylinder, for example (72), in order to restrict its movements within the limits required for the performance of the tests.

So as to facilitate the performance of tests over a wide range of angular and irregular surfaces—a number of flaw detector/probe versions are produced. One version comprises two hinges within every one of the bridges (7, 6) which allow a limited circular movement at an incline of about 10° relative to the vertical position of each of the separate converters (2, 3). In the various versions of the probe/detector (1)—the connection of the bridges (6, 7) to the bases (22, 32) is carried out through the covers (23, 33) of the radiator and the receiver (2, 3), so that the limited circular movement is of the converter covers (2, 3). Adjusting means allow for the control of the radiator and receiver (2, 3) positions to the type and conditions of a specific test. The connection between the bases (22, 32) and the covers (23, 33) of the radiator and the receiver (2, 3) is carried out through adjusting means (34) which enable a preferred position of the bases (22, 32) relative to the covers (23, 33).

When testing materials, such as metals, the tester presses the holder (5) and thus also presses the converters (2, 3) and each one of them receives the most appropriate angle for the surface component beneath it. Afterward, the device is slid over the product being tested, during which the device radiates ultrasonic rays and receives them.

I claim:

1. A device for revealing defects in materials and their connections by radiating ultrasonic energy and receiving that energy following its reflection from a product to be tested, comprising:

an ultrasonic energy radiator;

an ultrasonic energy receiver; and a base for directing ultrasonic energy while appearing substantially transparent thereto, said base having a curvilinear surface section on one side, and an opposite side to be directed toward the product to be tested;

wherein, at least one of said ultrasonic energy radiator and receiver comprises a system of interconnected sub-plates mounted to said curvilinear surface section of said base and approximating the shape thereof.

2. A device for revealing defects in materials and their connections according to claim 1, wherein each sub-plate is planar.

3. A device for revealing defects in materials and their connections according to claim 1, wherein said radiator and receiver comprise, respectively, first and second systems of interconnected sub-plates mounted to respective curvilinear surface sections of a common base, the first and second sub-plate systems approximating the shapes of the respective curvilinear surface sections, the first sub-plate system being arranged to transmit ultrasonic energy through said base to the product to be tested, and the second sub-plate system being arranged to receive ultrasonic energy reflected from the product and transmitted back through said base.

4. A device for revealing defects in materials and their connections according to claim 1, said radiator and receiver including first and second systems of interconnected sub-plates mounted to respective curvilinear surface sections of first and second separate bases, the first and second sub-plate systems approximating the shapes of the respective curvilinear surface sections, the first sub-plate system being arranged to transmit ultrasonic energy through the first base to the product to be tested, and the second sub-plate system being arranged to receive ultrasonic energy reflected from the product and transmitted back through said second base.

5. A device for revealing defects in materials and their connections according to claim 1, wherein the curvilinear surface section of the base is a cylindrical surface section oriented at an angle with respect to said opposite side.

6. A device for revealing defects in materials and their connections according to claim 9, in which each sub-plate system constitutes a converter of ultrasonic vibrations.

7. A device for revealing defects in materials and their connections according to claim 3, in which the two sub-plate systems are separated from each other by means of an ultrasonic shutter.

8. A device for revealing defects in materials and their connections according to claim 1, in which each system of interconnected sub-plates comprises at least two sub-plates.

9. A device for revealing defects in materials and their connections according to claim 8, in which each sub-plate is made of piezoelectric material.

10. A device for revealing defects in materials and their connections according to claim 9, in which each piezoelectric sub-plate is coated on both sides with a conductive envelope, for including each sub-plate in an electrical circuit.

11. A device for revealing defects in materials and their connections according to claim 10, in which each sub-plate system constitutes a series of planar, square or rectangular surfaces of piezoelectric sub-plates, fixed to a single base.

12. A device for revealing defects in materials and their connections according to claim 1, in which contact surfaces of the base, for contacting the product to be tested, are fortified by grooves filled with a wear-resistant material for increasing the device's resistance to wear and extending its service life.

13. A device for revealing defects in materials and their connections according to claim 12, in which the wear-resistant material is transparent to ultrasonic radiation.

14. A device for revealing defects in materials and their connections according to claim 13, in which a thickness of the wear resistant material layer in each groove is less than the ultrasonic wavelength in the bases of the systems.

15. A device for revealing defects in materials and their connections according to claim 11, in which the shaping of each sub-plate system on the base in the form of a cylindrical surface segment endows the panel with a required radiation focusing property.

16. A device for revealing defects in materials and their connections according to claim 15, in which the sub-plates are bonded to said curvilinear surface section.

17. A device for revealing defects in materials and their connections by radiating ultrasonic energy and receiving that energy following its reflection from a product to be tested, comprising:

an ultrasonic energy radiator;

an ultrasonic energy receiver; and a base;

wherein, at least one of said ultrasonic energy radiator and receiver comprises a system of interconnected sub-plates bonded to said base with at least two exposed metal wires installed between a lower coating of each sub-plate and the base.

18. A device for revealing defects in materials and their connections according to claim 17, in which the wires installed on the base are covered by the lower conductive coating of each piezoelectric sub-plate, which is electrically connected to grounding.

19. A device for revealing defects in materials and their connections according to claim 18, in which the parameters of each sub-plate system are adjustable by electronic means, so that each point on the panel is endowed with equal or variable parameters and properties, according to the requirements of a specific test.

20. A device for revealing defects in materials and their connections according to claim 19, in which each sub-plate system is connected to an electricity network by means of a transformer.

21. A device for revealing defects in materials and their connections according to claim 20, in which each sub-plate system is connected to the electricity network by means of its own auto-transformer, wherein each piezoelectric sub-plate is electrically connected to the mid-point of the auto-transformer.

22. A device for revealing defects in materials and their connections according to claim 21, in which an upper coating of each piezoelectric sub-plate is connected to the auto-transformer by electronic means.

23. A device for revealing defects in materials and their connections according to claim 22, in which the sub-plates in each system are interconnected in a parallel fashion through coordinating and adjustable resistors.

24. A device for revealing defects in materials and their connections according to claim 22, in which the sub-plates in each system are serially interconnected through coordinating and adjustable resistors.

25. A device for revealing defects in materials and their connections according to claim 22, in which the sub-plates in each system are interconnected by means of groups of coordinating and adjustable resistors, wherein the sub-plates in each group are serially interconnected, while the groups are interconnected in a parallel fashion.

26. A device for revealing defects in materials and their connections according to claim 1, in which the radiator and receiver are separated, each of them within its own cover, and they are joined together by means of a holder to form a single unit.

27. A device for revealing defects in materials and their connections according to claim 26, in which the radiator and the receiver are connected to the holder by means of bridges allowing precise tests to be carried out on angular and irregular surfaces.

28. A device for revealing defects in materials and their connections according to claim 27, in which the connection between one of the radiator and receiver, and the holder, is established by means of a fixed bridge, while the connection between the other of the radiator and receiver, and the holder, is established by means of a bridge with a hinge.

29. A device for revealing defects in materials and their connections according to claim 28, is constructed of two cylinders of different diameters, an external hollow cylinder and a solid inner cylinder.

30. A device for revealing defects in materials and their connections according to claim 29, wherein a small gap is left between the two cylinders, so as to enable one of the cylinders to turn within the other.

31. A device for revealing defects in materials and their connections according to claim 29, in which the movement of the inner cylinder within the external cylinder is limited.

32. A device for revealing defects in materials and their connections according to claim 31, in which a limitation of movement of the inner cylinder within the external cylinder is carried out by a rod connected to one of the cylinders which moves within a groove over the second cylinder.

33. A device for revealing defects in materials and their connections according to claim 27, in which each of the bridges has a hinge.

34. A device for revealing defects in materials and their connections according to claim 33, in which movement of at least one of the hinges is limited to an incline of about 10° relative to the vertical position of the radiator or receiver connected to the holder by means of the respective hinge.

35. A device for revealing defects in materials and their connections according to claim 27, in which the bridges are connected to the covers of the radiator and the receiver.

36. A device for revealing defects in materials and their connections according to claim 27, in which the base of each sub-plate system is connected to the covers of the radiator and the receiver through adjustable means.

37. A method for revealing defects in materials and their connections which includes the radiation of ultrasonic energy and the reception of that energy following its reflection from a tested product, wherein:
the radiation and reception of the ultrasonic energy takes place within a system of interconnected sub-plates by means of a signal connection of each of the sub-plates;
the parameters of each sub-plate are adjusted by electronic means, so that each point of the system is endowed with equal or variable parameters and properties according to the requirements of the specific test; and
the connection of each sub-plate's system to the power network is effected by its own auto-transformer.

38. A method for revealing defects in materials and their connections according to claim 37, wherein each sub-plate is bonded to a base.

39. A method for revealing defects in materials and their connections according to claim 39, in which the effect of static capacitance of the sub-plate system on the system's input parameters is decreased, thus increasing the sensitivity of the method through the use of an auto-transformer.

40. A method for revealing defects in materials and their connections according to claim 37, in which a radiating sub-plate system is separated from a receiving one, and each one of the sub-plate systems is installed within its own cover and joined into a single unit by means of a holder.

41. A method for revealing defects in materials and their connections according to claim 40, which allows more accurate tests to be carried out on angular and irregular surfaces, through the connection of the radiating part and the receiving pan to the holder by means of bridges.

42. A method for revealing defects in materials and their connections according to claim 41, in which at least one of the bridges is hinged, so as to allow circular movement of the converter connected to the holder by means of this hinge.

43. A method for revealing defects in materials and their connections according to claim 42, in which the movement of each hinge is limited.

44. A method for revealing defects in materials and their connections according to claim 43, in which the movement of each hinge is limited within the limits appropriate to the requirements of a certain test.

45. A method for revealing defects in materials and their connections according to claim 43 in which the movement of at least one of the hinges is limited to an incline of about 10° relative to the vertical position of the converter connected to the holder by means of this hinge.

46. A method for revealing defects in materials and their connections according to claim 40, in which the separate sub-plate systems each have a base which is capable of movement relative to its cover.

47. A method for revealing defects in materials and their connections according to claim 46, which allows for the adjusting of the positions of each of the sub-plate system bases in accordance with the conditions of a specific test by means of control and adjusting.

48. A method for revealing defects in materials and their connections according to claim 46, in which it is possible to move the radiator and the receiver relative to the holder by bridges with hinges.

49. A method for revealing defects in materials and their connections according to claim 48, which allows for the adjustment of the position of the radiator cover and the receiver cover in accordance with the conditions of a specific test by means of control and adjusting.

50. A method for revealing defects in materials and their connections according to claim 37, which includes the movement of a flaw detection device including said sub-plate system over the tested product, so that a contact surface of two bases of the device pass over the surface of the product and allow transfer of quality data.

* * * * *